(12) United States Patent
Huang et al.

(10) Patent No.: US 10,232,009 B1
(45) Date of Patent: Mar. 19, 2019

(54) PEPTIDE FOR PROMOTING WOUND HEALING, ITS COMPOSITION AND METHOD OF USING THE SAME

(71) Applicant: PRO SUNFUN BIOTECH RESEARCH AND DEVELOPMENT CO., LTD., Kaohsiung (TW)

(72) Inventors: Min-Chuan Huang, Taipei (TW); Syue-Ting Chen, Taipei (TW); Yu-Chun Liu, Taoyuan (TW)

(73) Assignee: PRO SUNFUN BIOTECH RESEARCH AND DEVELOPMENT CO., LTD., Kaohsiung (TW)

( * ) Notice: Subject to any disclaimer, the term of this patent is extended or adjusted under 35 U.S.C. 154(b) by 0 days.

(21) Appl. No.: 15/720,767

(22) Filed: Sep. 29, 2017

(51) Int. Cl.
| | |
|---|---|
| *A61K 38/08* | (2006.01) |
| *A61K 38/00* | (2006.01) |
| *C07K 7/06* | (2006.01) |
| *C07K 7/00* | (2006.01) |
| *A61K 38/02* | (2006.01) |
| *A61K 9/00* | (2006.01) |

(52) U.S. Cl.
CPC ............ *A61K 38/02* (2013.01); *A61K 9/0014* (2013.01)

(58) Field of Classification Search
CPC .......... A61K 38/08; A61K 38/00; C07K 7/06; C07K 7/00
USPC .......... 514/1.1, 18.6, 21.7, 9.4; 530/329, 300
See application file for complete search history.

(56) References Cited

U.S. PATENT DOCUMENTS 8,454,963 B2 * 6/2013 Tomlinson ........... C07K 14/705
424/178.1

OTHER PUBLICATIONS

A0A1X2GXV9 from UniProt, pp. 1-2. Integrated into UniProtKB/TrEMBL on Jul. 5, 2017.*

* cited by examiner

*Primary Examiner* — Julie Ha
(74) *Attorney, Agent, or Firm* — Birch, Stewart, Kolasch & Birch, LLP

(57) ABSTRACT

Disclosed is a peptide consisting of an amino acid sequence of HisThrSerThrGluAlaLys (SEQ ID NO: 1). This peptide is effective in the enhancement of fibroblast cell migration, which promotes wound healing. Also provided are a pharmaceutical composition for promoting wound healing comprising the peptide, and a method for promoting wound healing using the peptide.

6 Claims, 4 Drawing Sheets

Specification includes a Sequence Listing.

PEPTIDE FOR PROMOTING WOUND HEALING, ITS COMPOSITION AND METHOD OF USING THE SAME

REFERENCE TO SEQUENCE LISTING SUBMITTED VIA EFS-WEB

This application includes an electronically submitted sequence listing in .txt format. The .txt file contains a sequence listing entitled "2018-01-09_5992-0187PUS1_ST25.txt" created on Jan. 9, 2018 and is 626 bytes in size. The sequence listing contained in this .txt file is part of the specification and is hereby incorporated by reference herein in its entirety.

FIELD OF THE INVENTION

The present invention relates generally to a peptide effective for promoting wound healing, its composition and method of using the same.

BACKGROUND OF THE INVENTION

Wound healing requires the coordination of several cell types including keratinocytes, fibroblasts, endothelial cells, macrophages and platelets. The process involves cell proliferation and migration, collagen deposition and remodeling, wound contraction and angiogenesis. Fibroblasts are the most important cells involved in producing and remodeling the extracellular matrix, and fibroblast cell proliferation and migration play key roles in the formation of granulation tissue and further wound repair. Cell migration consisting of a multi-step cyclic process is necessary for wound repair. The basic migration pattern requires extension of a protrusion, stable attachment to near the leading edge of the protrusion, forward movement of the cell body and release of adhesions and retraction at the cell rear. (Lauffenburger and Horwitz. Cell migration: a physically integrated molecular process. Cell 84: 359-369, 1996.) Since fibroblast cell migration is very important during the wound healing, it may be used as an in vitro model for investigation of the effects on wound healing.

What would be advantageous is a non-toxic, non-antigenic, inexpensive wound-healing agent having the ability to promote wound healing and allow non-healing wounds to heal.

BRIEF SUMMARY OF THE INVENTION

It is unexpectedly found in the present invention that a peptide having the amino acid sequence of HisThrSerThrGluAlaLys (SEQ ID NO: 1) is effective in the enhancement of fibroblast cell migration, which is potential for promotion of wound healing.

Accordingly, the present invention provides in one aspect a synthetic peptide consisting of the amino acid sequence of SEQ ID NO: 1, which is also named as Peptide No. 9. The peptide provides an efficacy t in promotion of wound healing.

In another aspect, the present invention provides a cosmetic or pharmaceutical composition for promoting wound healing, comprising an effective amount of Peptide No. 9 and a cosmetically or pharmaceutically acceptable carrier.

In one further aspect, the present invention provides a method for promoting wound healing, which comprises administering to a subject in need thereof the peptide having the amino acid sequence of SEQ ID NO: 1 in an amount effective to enhance the migration of fibroblast cells in the subject.

In one embodiment of the method according to the invention, the peptide is topically administered to the subject.

It is to be understood that both the foregoing general description and the following description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1A:
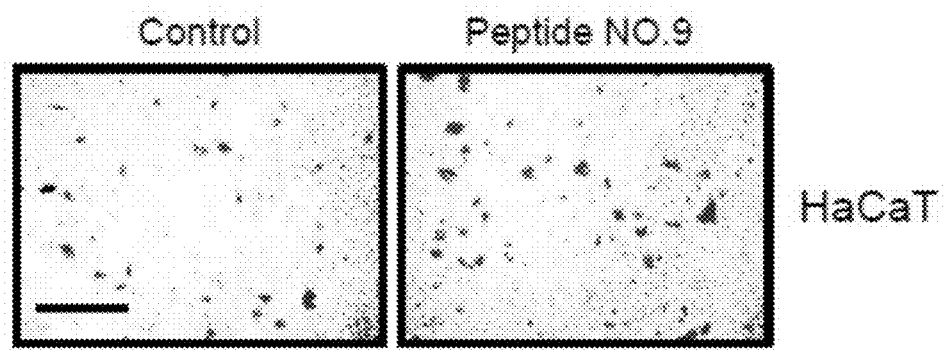
FIG. 1A provides the representative images of HaCaT keratinocyte cell migration after 24-hour culture with 50 μg/ml Peptide NO. 9 in transwell migration assay (Scale bar, 1 mm), showing that Peptide NO. 9 enhanced HaCaT keratinocyte cell migration.

Unless defined otherwise, all technical and scientific terms used herein have the same meaning as commonly understood by those of ordinary skill in the art to which this invention belongs.

The use of the word "a" or "an" when used in conjunction with the term "comprising" in the claims and/or the specification may mean "one," but it is also consistent with the meaning of "one or more," "at least one," and "one or more than one."

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. Standard abbreviations for amino acids are used.

As used herein, the term "subject" refers to a vertebrate or vertebrates, preferably mammals, including, for example, humans, laboratory animals such as rats and mice, and farm animals, such as horses and cows; particularly humans. Hereinafter, a human serving as a subject is specifically referred to as a "human subject."

As used herein, the term "carrier" or "cosmetically or pharmaceutically acceptable carrier" refers to any material commonly used on the formulations of cosmetic or pharmaceutical compositions used to enhance stability, sterility and deliverability. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. The compositions may contain physiologically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "systemic" or "systemically" as used herein refers to a route of administration of medication or other substance into the circulatory system so that the entire body of a subject to be administered is affected. The administration may take place via enteral administration (through which the absorption of the medication or other substance through gastrointestinal tracts) or parenteral administration such as injection, infusion or implantation.

The term "topical" or "topically" is used herein its conventional sense as referring to a spot which can be in or on any part of the body, including but not limited to the epidermis, any other dermis, or any other body tissue. Topical administration or application means the direct contact of the peptide with tissue, such as skin or membrane which contains melanin-producing cells.

The term "effective amount" as used herein refers to a sufficient amount of the peptide according to the invention to provide desired therapeutic or cosmetic effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation. For example, the peptide according to the invention may be administered systemically, transdermally or topically.

The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof. In addition to standard carriers, a pharmaceutical composition of the present invention may be supplemented with one or more excipients that are normally employed in common standard formulations, such as surfactants, solubilizers, stabilizers, emulsifiers, thickeners, and preservatives. Such excipients are well known to those skilled in the art.

As shown in the examples, the peptide having the amino acid sequence of SEQ ID NO: 1, which may be artificially synthesized by a standard method or in any manner commonly used or known to one of ordinary skill. It was confirmed to have an effect in enhancing the expression of keratinocyte cells, and the migration of the fibroblast cells. Therefore, the invention also provides a method for promoting wound healing, which comprises administering to a subject in need thereof the peptide having the amino acid sequence of SEQ ID NO: 1 in an amount effective to enhance the expression of collagen or elastin in fibroblast cells, and the migration of the fibroblast cells.

The pharmaceutical composition of the present invention may be constituted with one or more pharmaceutically acceptable carriers into any form suitable for the mode of administration selected, including systemic and topical administrations via enteral or parenteral administration such as injection, infusion or implantation, oral, transdermal or topical administration. In certain embodiments of the invention, the composition may be formulated with a pharmaceutically or cosmetically acceptable carrier as a topical formulation in a solution, ointment, gel, serum, cream, lotion, powder, emulsion or any form for administration. In some particular examples, the formulation may be administered via a spray device, a dressing, or a paste.

The present invention is further illustrated by the following examples, which are provided for the purpose of demonstration rather than limitation.

EXAMPLES

Example 1: Preparation of the Peptide of SEQ ID NO: 1

The peptide consisting of the sequence of SEQ ID NO: 1 (HisThrSerThrGluAlaLys) was synthesized by MDBio, Inc. (Taipei, Taiwan) and the purity and composition of peptide was confirmed by high performance liquid chromatography (HPLC) and mass spectrometry. Peptide stock was stored at −20° C. after dissolving 10 mg of lyophilized peptide powder in 250 μl of double deionized water (dd $H_2O$).

Example 2: Cell Culture

Human keratinocyte HaCaT and skin fibroblast CCD-966SK cells were cultured in Dulbecco's Modified Eagle Medium (DMEM) containing 10% (v/v) FBS and 1% (v/v) antibiotics in 5% $CO_2$ at 37° C.

Example 3: Transwell Migration Assay

HaCaT cells ($5 \times 10^4$) or CCD-966SK cells ($5 \times 10^3$) in 0.25 ml serum-free DMEM were seeded into the upper chamber with an 8-μm pore size membrane (Corning, USA) and 0.5 ml serum free DMEM with or without 50 μg/ml Peptide NO. 9 were loaded to the lower chamber in 24-well culture plate. After 24 hours incubation, cells were fixed and stained with 0.5% (w/v) crystal violet (Sigma) containing 20% (v/v) methanol. The number of migrated cells from 5 random fields was counted under the microscope. Results obtained were analyzed by student's t-test and graphed as mean±SD.

Figure 1B:
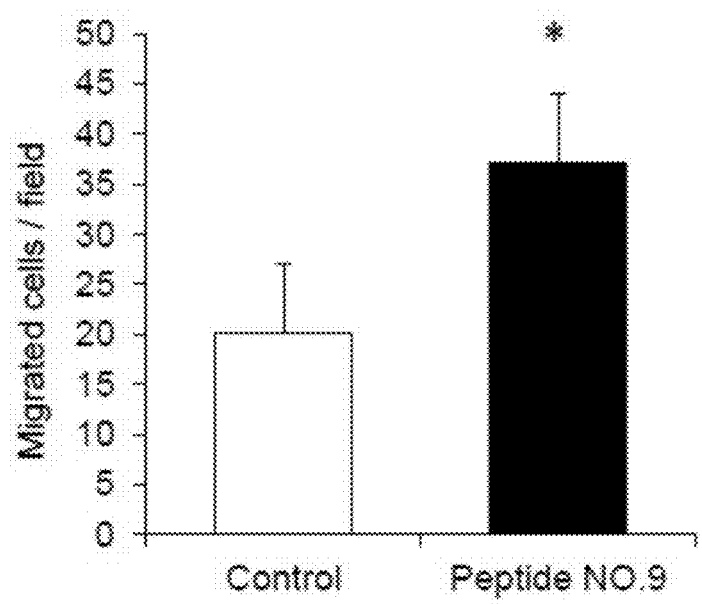
FIG. 1B provides the result of the statistic analysis of HaCaT keratinocyte cell migration after 24-hour culture with 50 μg/ml Peptide NO. 9 in transwell migration assay ($*P<0.05$), showing that Peptide NO. 9 provided a significant efficacy in enhancing HaCaT keratinocyte cell migration.

The results were shown in FIG. 1A and FIG. 1B. As shown in FIG. 1A providing representative images of HaCaT keratinocyte cell migration after 24-hour culture with 50 μg/ml Peptide NO. 9, and FIG. 1B providing the result of the statistic analysis, Peptide NO. 9 provided an effect in enhancement of keratinocyte cell migration of HaCaT cells (P<0.05).

Figure 2A:
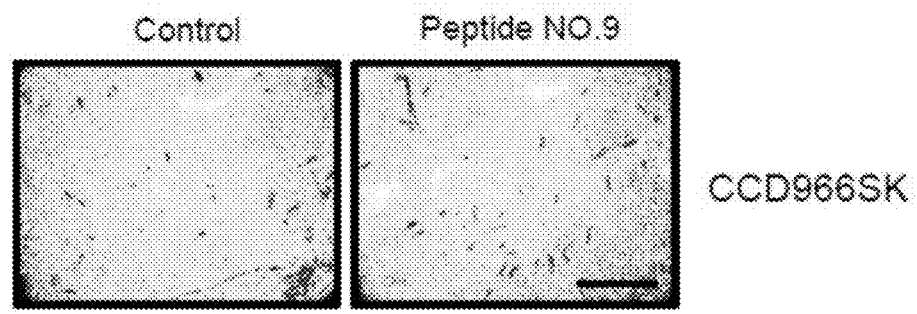
FIG. 2A provides representative images of CCD966SK fibroblast cell migration after 24-hour culture treated with 50 μg/ml Peptide NO. 9 in transwell migration assay, showing that Peptide NO. 9 enhanced CCD966SK fibroblast cell migration.
Figure 2B:
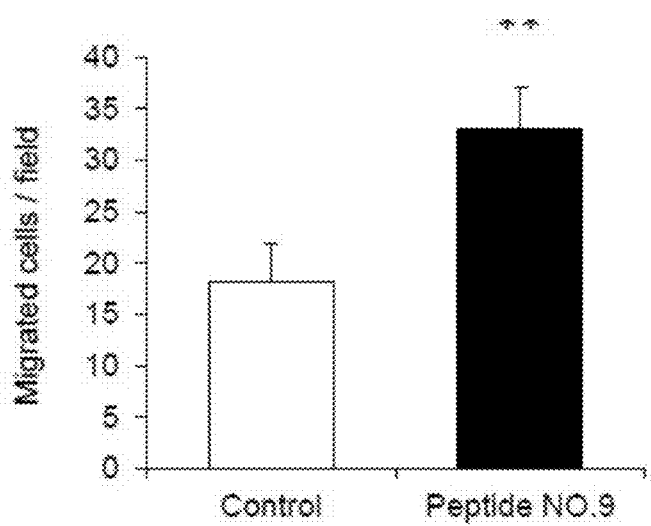
FIG. 2B provides the results of the statistic analysis of migration after 24-hour culture treated with 50 μg/ml Peptide NO. 9 in transwell migration assay ($**P<0.01$), showing that Peptide NO. 9 provided a significant efficacy in enhancing HaCaT CCD966SK fibroblast cell migration.

It is also illustrated in FIGS. 2A and 2B that Peptide NO. 9 enhanced CCD966SK fibroblast cell migration. As shown in FIG. 2A providing representative images of CCD966SK fibroblast cell migration after 24-hour culture with 50 μg/ml Peptide NO. 9 in transwell migration assay, and FIG. 2B showing that the Peptide NO. 9 provided an effect in enhancement of keratinocyte cell migration of CCD966SK cells (P<0.01).

Example 4: MTT Assay

HaCaT keratinocyte cells (3×10³, each cell line) in 100 μl complete DMEM were seeded in 96-well plates with or without 50 μg/ml Peptide NO. 9, respectively. Ten microliters of 5 mg/ml 3-(4,5-dimethyl-2-thiazolyl)-2,5-diphenyl-2H-tetrazolium bromide solution (MTT; Sigma) was added to each well for the indicated times and incubated at 37° C. for 3 hours, after which 100 μl 10% SDS in 0.01 N HCl was added to dissolve the MTT formazan crystals. The resultant optical density was measured spectrophotometrically at dual wavelengths, 550 and 630 nm.

Figure 3A:
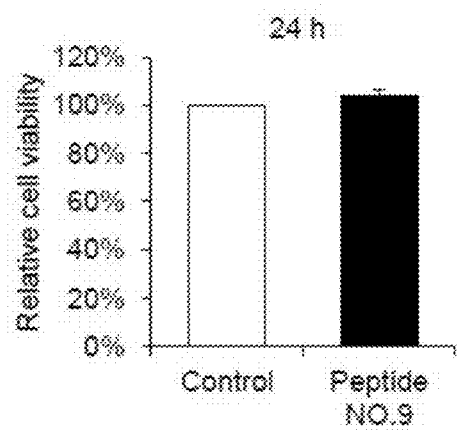
FIG. 3A provides the viability of HaCaT keratinocyte cells after 24-hour culture treated with 50 μg/ml Peptide NO. 9 in MTT assay, indicating that Peptide NO. 9 did not significantly affect viability of HaCaT cells.
Figure 3B:
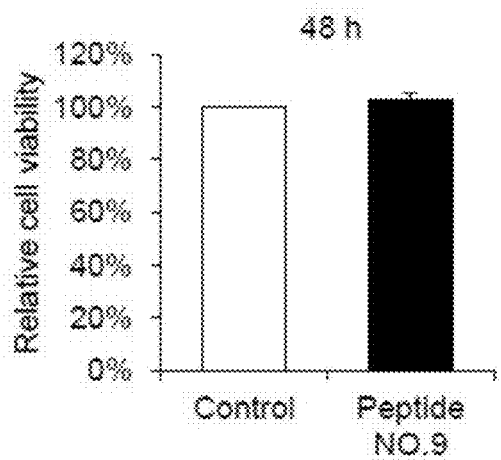
FIG. 3B provides the viability of HaCaT keratinocyte cells after 48-hour culture treated with 50 μg/ml Peptide NO. 9 in MTT assay, indicating that Peptide NO. 9 did not significantly affect viability of HaCaT cells.
Figure 3C:
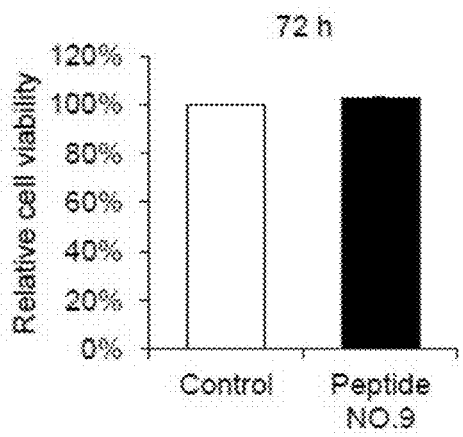
FIG. 3C provides the viability of HaCaT keratinocyte cells after 72-hour culture treated with 50 μg/ml Peptide NO. 9 in MTT assay, indicating that Peptide NO. 9 did not significantly affect viability of HaCaT cells.

The viability of HaCaT keratinocyte cells after 24-hour, 48-hour or 72-hour culture treated with 50 μg/ml Peptide NO. 9 were tested by MTT assay. As shown in FIG. 3A (for 24 hour), FIG. 3B (for 48 hour) and FIG. 3C (for 74 hour), Peptide NO. 9 did not significantly affect viability of HaCaT cells.

Figure 4A:
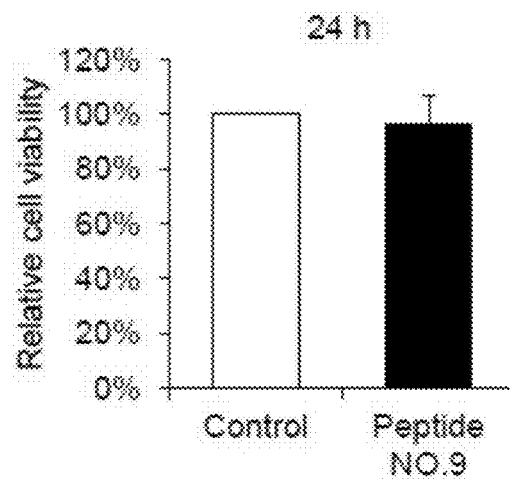
FIG. 4A shows the viability of CCD966SK cells which were treated with 50 μg/ml Peptide NO. 9 for 24 hours, indicating that Peptide NO. 9 did not significantly affect viability of CCD966SK cells.

In the same manner, the viability of CCD966SK keratinocyte cells after 24-hour culture FIG. 4A shows the viability of CCD966SK cells which were treated with 50 μg/ml Peptide NO. 9 for 24 hours, indicating that Peptide NO. 9 did not significantly affect viability of CCD966SK cells.

Figure 4B:
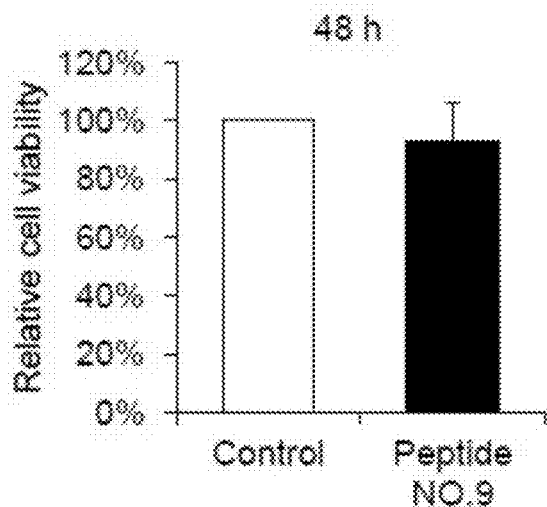
FIG. 4B shows the viability of CCD966SK cells which were treated with 50 μg/ml Peptide NO. 9 for 48 hours, indicating that Peptide NO. 9 did not significantly affect viability of CCD966SK cells.

FIG. 4B shows the viability of CCD966SK cells which were treated with 50 μg/ml Peptide NO. 9 for 48 hours, indicating that Peptide NO. 9 did not significantly affect viability of CCD966SK cells.

Figure 4C:
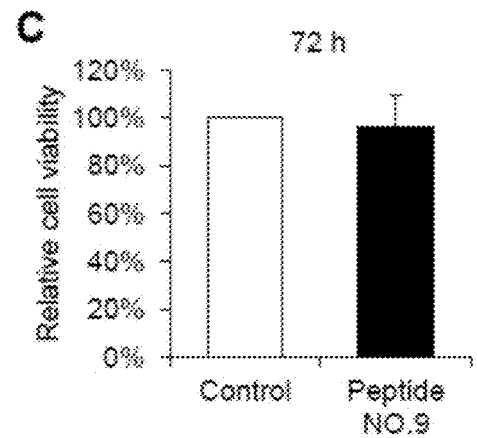
FIG. 4C shows the viability of CCD966SK cells which were treated with 50 μg/ml Peptide NO. 9 for 72 hours, indicating that Peptide NO. 9 did not significantly affect viability of CCD966SK cells.

FIG. 4C shows the viability of CCD966SK cells which were treated with 50 μg/ml Peptide NO. 9 for 72 hours, indicating that Peptide NO. 9 did not significantly affect viability of CCD966SK cells.

Given the above, it is concluded that the peptide according to the invention (i.e., Peptide No. 9) provides an unexpected efficacy in promotion of wound healing through the enhancement of fibroblast cell migration, instead of fibroblast cell viability.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A pharmaceutical composition for wound healing, comprising
   a synthetic peptide consisting of the amino acid sequence of SEQ ID NO: 1 in an amount effective to enhance fibroblast cell migration and a pharmaceutically acceptable carrier.

2. The pharmaceutical composition of claim 1, wherein the composition is for systemic, transdermal or topical administration.

3. The pharmaceutical composition of claim 2, wherein the composition is for topical administration.

4. The pharmaceutical composition of claim 3, which is in a form of an ointment, gel, or emulsion.

5. The pharmaceutical composition of claim 3, wherein the composition is for topical administration via a spray device, a dressing or a paste.

6. A method for promoting wound healing, which comprises administering to a subject in need thereof the composition of claim 1.

* * * * *

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

His Thr Ser Thr Glu Ala Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Pro Asp Ser Thr Glu Ala Lys
1               5
```